US006043411A

United States Patent [19]

Nishizawa et al.

[11] Patent Number: 6,043,411

[45] Date of Patent: Mar. 28, 2000

[54] GENE FOR FATTY ACID DESATURASE, VECTOR CONTAINING SAID GENE, PLANT TRANSFORMED WITH SAID GENE, AND PROCESS FOR CREATING SAID PLANT

[75] Inventors: Osamu Nishizawa; Toshihiro Toguri, both of Kanagawa, Japan

[73] Assignee: Kirin Beer Kabushiki Kaisha, Tokyo, Japan

[21] Appl. No.: 08/663,082

[22] PCT Filed: Dec. 28, 1994

[86] PCT No.: PCT/JP94/02288

§ 371 Date: Jun. 25, 1996

§ 102(e) Date: Jun. 25, 1996

[87] PCT Pub. No.: WO95/18222

PCT Pub. Date: Jul. 6, 1995

[30] Foreign Application Priority Data

Dec. 28, 1993 [JP] Japan .................................... 5-352858

[51] Int. Cl.[7] .............................. A01H 5/00; C12N 5/04; C12N 15/82

[52] U.S. Cl. ......................... 800/289; 800/298; 536/23.2; 435/419; 435/468

[58] Field of Search .................................... 800/205, 289, 800/281, 298; 536/23.1, 23.2; 435/419, 172.3, 69.1, 320.1, 468

[56] References Cited

U.S. PATENT DOCUMENTS 5,639,645 6/1997 Murata ................................ 435/252.3

FOREIGN PATENT DOCUMENTS

| | | |
|---|---|---|
| 0 561 569 A2 | 3/1993 | European Pat. Off. . |
| 0 550 162 | 7/1993 | European Pat. Off. . |
| 0 644 263 | 3/1995 | European Pat. Off. . |
| PCT/JP92/0002 | 9/1992 | Japan . |
| 245 367 | 8/1994 | New Zealand . |
| 91/13972 | 9/1991 | WIPO . |

OTHER PUBLICATIONS

Polashock et al. Plant Physiol 100: 894–901, Oct. 1992.

Ishizaki–Nishizawa et al., "Low–Twmperature Resistance of Higher Plants is Significantly Enhanced By A Nonspecific Cyanobacterial Desaturase", *Nature Biotechnology,* vol. 14:1003–1006, (1996).

Shanklin et al., "Stearoyl–acyl–carrier–protein Desaturase From Higher Plants Is Structurally Unrelated To The Animal And Fungal Homologs", *Proc. Natl. Acad. Sci. USA,* vol. 88:2510–2514, (1991).

J. F. Santaren et al., "Thermal and $^{13}C$–NMR Study of the Dynamic Structure of 1–Palmitoyl–2–Oleyl–$_{an}$–Glycero–3–Phosphocholine and 1–Oleyl–2–Palmitoyl–$_{an}$–Glycero–3–Phosphocholine in Aqueous Dispersions", Biochimica et Biophysica Acta vol. 687, 1982, pp. 231–237.

N. Murata et al., "Compositions and Positional Distributions of Fatty Acids in Phospholipids from Leaves of Chilling–Sensitive and Chilling–Resistant Plants", Plant and Cell Physiol., vol. 23, No. 6, 1982, pp. 1071–1079.

P. G. Roughan, "Phosphatidylglycerol and Chilling Sensitivity in Plants", Plant Physiol., vol. 77 1985, pp. 740–746.

M. Frentzen et al., Specificities and Selectivities of Glycerol–3–Phosphate Acyltransferase and Monoacylglycerol–3–Phosphate Acyltranferase from Pea and Spinach Chloroplasts, Eur. J. Biochem. vol. 129, pp. 629–636.

N. Murata, "Molecular Species Composition of Phosphatidylglycerols from Chilling–Sensitive and Chilling Resistant Plants", Plant and Cell Physiol. vol. 24, No. 1, 1983, pp. 81–86.

M. Frentzen et al., "Properties of the Plastidal Acyl–(Acyl–Carrier–Protein): Glycerol–3–Phosphate Acyltransferase from the Chilling–Sensitive Plant Squash (Cucurbita moschata)", Plant ell Physiol., vol. 28, No. 7, 1987, pp. 1195–1201.

S. Toriyama et al, "Prominent Difference of Glycerolipids among Anther Walls, Pollen Grains and Leaves of Rice and Maize", Plant Cell and Physiol. vol. 29, No. 4, 1988, pp. 615–621.

T. Ono et al., "Chilling Susceptibility of the Blue–Green Alga Anacycstis nidulans", Plant Physiol., vol. 67, No. 1981, pp. 176–181.

H. Wada et al., "Synechocystis PCC6803 Mutants Defective in Desaturation of Fatty Acids", Plant Cell Physiol., vol. 30, No. 7, pp. 971–978.

H. Wada et al., "Enhancement of Chilling Tolerance of a Cyanobacterium by Genetic Manipulation of Fatty Acid Desaturation", Nature, vol. 347, No. 6289, pp. 200–203.

A. Reddy et al., "Isolation of A $\Delta^6$ desaturase Gene from the Cyanobacterium Synechocystis sp. Strain PCC 6803 by Gain–of–Funtion Expression in Anabaena sp. Strain PCC 7120", Plant Molecular Biology, vol. 27, 1993, pp. 293–300.

K. H. Kaestner et al, "Differentiation–Induced Gene Expression in 3T3–L1 Preadipocytes", Journal of Biology Chemistry, vol. 264, No. 25, Sep. 1989, pp. 14755–14761.

K. Mihara, "Structure and Regulation of Rat Liver Microsomal Stearoyl–CoA Desaturase Gene", J. Biochem, vol. 108, 1990, 1022–1029.

J. Stukey et al., The OLE1 Gene of Saccharomyces cerevisiae Encodes the Δ9 Fatty Acid Desaturase and Can Be Functionally Replaced by the Rat Stearoyl–CoA Desaturase Gene, J. Bio. Chem., vol. 265, No. 33, Nov. 1990, pp. 20144–20149.

(List continued on next page.)

*Primary Examiner*—Elizabeth F. McElwain
*Attorney, Agent, or Firm*—Foley & Lardner

[57] ABSTRACT

Genes encoding proteins having an activity of desaturating lipid-bound fatty acids at the Δ9 position; vectors which contain the genes or polynucleotides containing part of thereof; plant cells transformed with the genes or polynucleotides containing part of thereof; a method for creating plants by regenerating the plant cells to reproduce mature plants; and plants transformed with the genes or polynucleotides containing part of thereof.

9 Claims, 5 Drawing Sheets

OTHER PUBLICATIONS

N. S. Yadav et al., Cloning of Higher Plant ω–3 Fatty Acid Desaturases, Plant Physiol. (1993) vol. 103, pp. 467–476.

N. Murata et al., "Modes of Fatty–Acid Desaturation in Cyanobacteria", Plant Cell Physiol., vol. 33, No. 7, 1992, pp. 933–941.

N. Sato et al., "Lipid Biosynthesis in the Blue–Green Alga, Anabaena Variabilis", Biochimica et Biophysia Acta, vol. 710, (1982), pp. 279–289.

D. G. Bishop et al., "Thermal Properties of Membrane Lipids from Two Cyanobacteria, Anacystis nidulans and Synechococcus sp.", Plant Cell Physiol., vol. 27, No. 8, pp. 1593–1598.

H. Wade et al., "The desA Gene of the Cyanobacterium Synechocystis sp. Strain PCC6803 is the Structural Gene for Δ12 Desaturase", Journal of Bacteriology, vol. 175, No. 18, Sep. 1993, pp. 6056–6058.

M. Bevan., "Binary Agrobacterium vectors for Plant Transformation", Nucl. Acids Res., vol. 12, No. 22, 1984, pp. 8711–8421.

V. A. Dzelzhalns et al., "The Molecular Biology of Cyanobacteria", Plant Molecular Biology, Shaw, C. H. ed., IRL Press, 1988.

T. Sakamoto et al., "Molecular Cloning of Δ12 Desaturase Gene from a Filamentous Cyanobacterium", Lecture Abstract No. 3aF04, 1993 Annual Meeting—The Japanese Society of Plant Physiologists.

P.H. Schreier et al, "The Use of Nuclear–Encoded Sequences to Direct the Light Regulated Synthesis and Transport of a Foreign Protein into Plant Chloroplasts", The EMBO Journal, vol. 4, No. 1, 1985, pp. 25–32.

FIG. 1

```
                  10        20        30        40        50        60
des9var    ALGLLLLYLGGWSFVVWGVFFRIVWVYHCTWLVNSATHKFGYRTYDAGDRSTNCWWVAVL
                            ..:.: . : . X::::::.: .:::.::    :     :
MSCD2      LVPWYCWGETFVNSLCVSTFLRYAVVLNATWLVNSAAHLYGYRPYDKNISSRENILVSMG
                 240       250       260       270       280       290

des9var    VFGEG
             :X
MSCD2      AVGER
```

FIG. 4

```
                        10        20        30        40        50        60
des9nid         MTLAIRPKLAFNWPTALFMVAIHIGALLAFLPANFNWPAVGVMVALYYITGCFGITLGWH
                      X::.. :.. ..:. .:.::: ..  .      . ... :::....:::  : :
MSCD2           DDEGPPPKLEYVWRNIILMALLHLGALYGITLVPSCKLYTCLFAYLYYVISALGITAGAH
               60        70        80        90       100       110

                        70        80        90       100       110       120
des9nid         RLISHRSFEVPKWLEYVLVFCGTLAMQHGPIEWIGLHRHHHLHSDQDVDHHDSNKGFLWS
                :: :::....   :   :.. .:.:.:..  ::   :: ::  :. ..:.:.:..::..:
MSCD2           RLWSHRTYKARLPLRLFLIIANTMAFQNDVYEWARDHRAHHKFSETHADPHNSRRGFFFS
              120       130       140       150       160       170

                       130        140       150       160       170
des9nid         HFLW-MIYEIPA-RTEVDKFTRDIAGDPVYRFFNKYFFGVQVLLGVLLYAWGEAWVGNGW
                X  : .. . :: ... .:....   .    .:.. ..  ..::  .. .   .:   :
MSCD2           HVGWLLVRKHPAVKEKGGKLDMSDLKAEKLVMFQRRYYKPDLLLMCFVLPTLVPWYCWGE
              180       190       200       210       220       230

              180          190       200       210       220       230
MSCD2           SFV---VWGIFARLVVVYHVTWLVNSATHKFGYRSHESGDQSTNCWWVALLAFGEGWHNN
                .::     ..: : .:: ..:::::::.: .:::.....  : .   :.. : :: .::
MSCD2           TFVNSLCVSTFLRYAVVLNATWLVNSAAHLYGYRPYDKNISSRENILVSMGAVGERFHNY
              240       250       260       270       280       290

                 240       250       260       270
des9nid         HHAYQYSARHGLQWWEFDLTWLIICGLKKVGLARKIKVASPNN
                :::..:. . .  .:....: ..:  .  . .:::
MSCD2           HHAFPYDYSASEYRWHINFTTFFIDCMALLGLAYDRKRVSRAA
              300       310       320       330       340
```

GENE FOR FATTY ACID DESATURASE, VECTOR CONTAINING SAID GENE, PLANT TRANSFORMED WITH SAID GENE, AND PROCESS FOR CREATING SAID PLANT

TECHNICAL FIELD

The present invention relates to genes encoding proteins having an activity of desaturating lipid-bound fatty acids at the Δ9 position (hereinafter referred to as "Δ9 desaturases"), vectors containing said genes, plants transformed with said genes and process for creating said plants.

BACKGROUND ART

The condition of membrane lipids which compose the biomembranes of organisms changes from liquid crystal to solid in accordance with the decrease in external temperatures. This change is called "phase separation". The phase separation involve change in properties of biomembranes. It is believed that membrane lipids lose the selectivity of mass permeability in solid conditions, making it impossible for biomembranes to carry out their essential functions and that, as a result, cells receive an injury (low temperature injury).

The phase transition temperatures of membrane lipids, at which the condition of the membrane lipids changes from liquid crystal to solid, are chiefly dependent on the degree of unsaturation (the number of double bonds in carbon chains) of fatty acid acyl groups bound to lipids. A lipid molecular species in which two bound fatty acid acyl groups are both saturated fatty acid residues has a higher phase transition temperature than room temperature, whereas a lipid molecular species having at least one double bond in bound fatty acid acyl groups has a phase transition temperature below about 0° C. (Santaren, J. F. et al., Biochim. Biophys. Acta, 687:231, 1982).

In general, the position of a double bond in a fatty acid is indicated after the symbol "Δ" by the number of carbons from the carboxyl terminus to the carbon having the double bond. The total number of double bonds is indicated after a colon following the total number of carbons. For example, linoleic acid is designated as 18:2 Δ9,12, which is represented by the following structural formula:

$$CH_3(CH_2)_4CH{=}CHCH_2CH{=}CH(CH_2)_7COOH$$

In some cases, the position of a double bond is indicated after the symbol "ω" by the number of carbons from the methyl terminus of a fatty acid to the carbon having the double bond.

Among the membrane lipids of higher plants, only phosphatidylglycerol (PG) contains a relatively large number of saturated molecular species and it has been strongly suggested that the phase transition of PG is responsible for low temperature injury in plants (Murata, N. et al., Plant Cell Physiol., 23:1071, 1982; Roughan, P. G., Plant Physiol., 77:740, 1985) and that the molecular species composition of PG is determined by the substrate specificity of glycerol-3-phosphate acyl transferase (hereinafter referred to as "ATase") present in chloroplasts (Frentzen, M. et al., Eur. J. Biochem., 129:629, 1983; Murata, N., Plant Cell Physiol., 24:81, 1983; Frentzen, M. et al., Plant Cell Physiol., 28:1195, 1988).

Nishizawa et al. showed that if an ATase gene obtained from *Arabidopsis thaliana* Heynhold, a plant resistant to chilling, was introduced and expressed in tobacco, the content of saturated molecular species of PG decreased, thereby imparting a higher chilling resistance to the tobacco than when it was of a wild type (PCT/JP92/00024, 1992). However, the ATase exists originally in plants and even if a large amount of an exogenous ATase is expressed in plants, it will compete inevitably with the endogenous ATase and its effect is therefore likely to be diluted. For example, the content of saturated molecular species of PG was about 28% in the leaf of a clone which expressed the largest amount of ATase from *Arabidopsis thaliana* Heynhold out of the created tobacco transformants, which content was lower by about 8% than in the wild-type tobacco and higher by about 8% than in the wild-type *Arabidopsis thaliana* Heynhold (PCT/JP92/00024, 1992).

In general, the majority of acyl-ACP produced in plastids consists of 16:0-ACP and 18:1-ACP, and their proportions are believed to be equal. In some tissues, the proportions of 16:0-ACP and 18:0-ACP may be higher than that of 18:1-ACP (Toriyama, S. et al., Plant Cell Physiol., 29:615, 1988). In these tissues, it may be difficult to reduce satisfactorily the content of saturated molecular species by using an exogenous ATase.

The composition of membrane lipids in photosynthetic cyanobacteria (blue-green algae) is similar to that of lipids in membrane systems composing higher plant's chloroplasts (Murata, N. et al., in "The Biochemistry of Plants", Academic Press, 1987). In blue-green algae, the degree of unsaturation of fatty acids bound to membrane lipids is controlled by enzymes capable of desaturating lipid-bound fatty acids. It is known that *Anacystis nidulans* (Synechococcus PCC 7942) which can introduce only one double bond into lipid-bound fatty acids is sensitive to chilling (Ono, T. et al., Plant Physiol., 67:176, 1981), whereas Synechocystis PCC6803 which can introduce at least two double bonds is resistant to chilling (Wada, H. et al., Plant Cell Physiol., 30:971, 1989).

All the desaturases of fatty acids in blue-green algae react with lipids as substrates to introduce a double bond into lipid-bound fatty acids. Therefore, a cis-type double bond can be introduced into fatty acids such as PG, SQDG, MGDG and DGDG in membrane lipids of blue-green algae, which are composed of 16:0/16:0- and 18:0/16:0-saturated molecular species (Murata, N. et al., in "The Biochemistry of Plants", Academic Press, 1987). In this respect, blue-green algae are very much different from higher plants that have fatty acid desaturases capable of introducing a double bond into stearoyl-ACP (18:0-ACP) at the Δ9 position and which never introduce a cis-type double bond into PG or SQDG after the synthesis of these lipids, which are composed of 16:0/16:0- (and a little amount of 18:0/16:0-) as saturated molecular species.

At present, it is known that the introduction and expression of the Δ12 desaturase gene of Synechocystis PCC6803 in *Anacystis nidulans* enables the production of 16:2 Δ9,12 which is not inherently present in the *Anacystis nidulans,* thereby imparting a chilling resistance to the *Anacystis nidulans* which is essentially chilling-sensitive (Wada, H. et al., Nature, 347:200, 1990).

Genes so far obtained for desaturases of blue-green algae include a Δ6 desaturase gene (Reddy, A. S. et al., Plant Mol. Biol., 27:293, 1993) and a Δ12 desaturase gene (Wada, H. et al., Nature, 347:200, 1990). However, the Δ6 and Δ12 desaturases cannot desaturate fatty acids at the Δ6 and Δ12 positions, respectively, unless a double bond is introduced at the Δ9 position. Moreover, Δ15 desaturase cannot desaturate fatty acids at the Δ15 position unless the fatty acids are desaturated at both the Δ9 and 12 positions. Hence, if the genes for enzymes capable of desaturating fatty acids at the Δ9 position are introduced and expressed in higher plants, they should be able to reduce the content of saturated molecular species in higher plants and thereby impart a chilling resistance to the higher plants. However, no gene for enzymes capable of desaturating fatty acids at the Δ9 position has been obtained until now.

Therefore, an object of the present invention is to provide genes for enzymes capable of desaturating fatty acids at the Δ9 position and polynucleotides containing part of said genes.

Another object of the present invention is to provide vectors which contain genes for enzymes capable of desaturating fatty acids at the Δ9 position or polynucleotides containing part of the genes.

A further object of the present invention is to provide plant cells and plants which are transformed with genes for enzymes capable of desaturating fatty acids at the Δ9 position or polynucleotides containing part of the genes.

DISCLOSURE OF THE INVENTION

As a result of various studies conducted to achieve the above objects, the inventors succeeded in cloning a gene encoding a Δ9 desaturase from genomic DNA of blue-green alga belonging to the genus Anacystis, obtaining vector DNA incorporating the gene, transforming a plant cell with the vector DNA, differentiating the cell to regenerate the plant, thereby imparting a chilling resistance to the plant. The present invention was accomplished on the basis of these findings. The subject matters of the present invention are as follows:

(1) Genes encoding proteins having an activity of desaturating lipid-bound fatty acids at the Δ9 position.

(2) The genes of (1) or polynucleotides containing part thereof, wherein the proteins having an activity of desaturating lipid-bound fatty acids at the Δ9 position contain the amino acid sequence substantially shown in SEQ ID NO: 4.

(3) The genes of (1) or polynucleotides containing part of thereof, wherein the genes encoding proteins having an activity of desaturating lipid-bound fatty acids at the Δ9 position are DNA chains containing the base sequence of SEQ ID NO: 3.

(4) Vectors which contain the genes or polynucleotides containing part of thereof according to any one of (1)–(3).

(5) Plant cells transformed with the genes or polynucleotides containing part of thereof according to any one of (1)–(3).

(6) A method for creating plants by differentiating the plant cells of (5) to regenerate plants.

(7) Plants transformed with the genes or polynucleotides containing part of thereof according to any one of (1)–(3).

BRIEF DESCRIPTION OF THE DRAWINGS

FIG. 1 shows the amino acid sequence encoded by des 9 var fragment as compared with the amino acid sequence of mouse stearoyl-CoA desaturase (MSCD2). In FIG. 1, : indicates that the two sequences have the same amino acids and • indicates that the two sequences have amino acids having similar properties. X shows a range of high homology.

FIG. 4 shows the amino acid sequences of des 9 nid as compared with the amino acid sequence of mouse stearoyl-CoA desaturase (MSCD2). The comparison was made in the same manner as in FIG. 1.

PREFERRED EMBODIMENTS OF CARRYING OUT THE INVENTION

Figure 2:
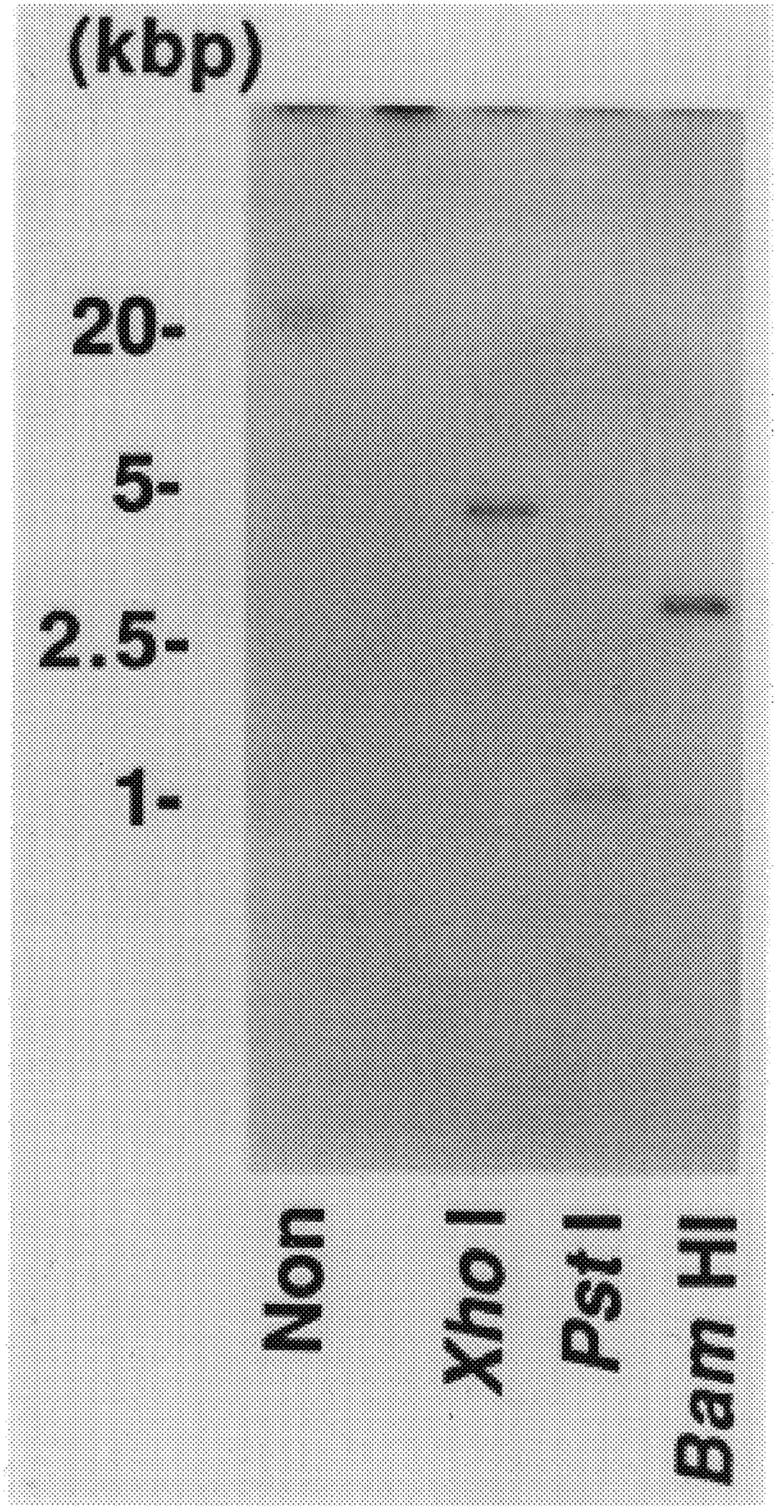
FIG. 2 is an electropherogram showing an autoradiogram in a Southern analysis of genomic DNA of *Anacystis nidulans* with des 9 var fragment used as a probe.

The Δ9 desaturase of the present invention is an enzyme which is inherently present in blue-green algae as described above in the BACKGROUND ART. The chemical structure of the Δ9 desaturase has local similarities to those of the stearoyl-CoA desaturases of mouse (Kaestner, K. H. et al., J. Biol. Chem., 264:14755, 1989), rat (Mihara, K., J. Biochem., 108:1022, 1990) and yeast (Stukey, J. E. et al., J. Biol. Chem., 265:20144, 1990) but it is very different taken as a whole. In addition, it is entirelly dissimilar to the chemical structures of known blue-green algal enzymes capable of desaturating lipid-bound fatty acids at the Δ6 and Δ12 positions and that of a higher plant enzyme capable of desaturating lipid-bound fatty acids at the ω3 position (Yadav, N. S. et al., Plant Physiol., 103:467, 1993). In the case where the genes of the present invention are produced from natural materials, blue-green algae may be used as raw materials. The blue-green algae to be used include but are not limited to those belonging to the genera Anacystis, Synechocystis, Anabaena and the like. In order to desaturate saturated molecular species in higher plants, Anacystis-type Δ9 desaturase (Murata, N. et al., Plant Cell Physiol., 33:933, 1992, Group 1-type blue-green algae belong to the genus Anacystis) is preferred to Anabaena- and Synechocystis-types for the following reason.

The sn-1 and sn-2 positions of almost all membrane lipids of Synechocystis PCC6803 and *Anabaena variabilis* are occupied by fatty acids of 18 carbon atoms (C18) and 16 carbon atoms (C16), respectively (Sato, N. et al., Biochim. Biophys. Acta, 710:279, 1982; Wada, H. et al., Plant Cell Physiol., 30:971, 1989). On the other hand, the both sn-1 and sn-2 positions of almost all membrane lipids of *Anacystis nidulans* are occupied by C16 (Bishop, D. G. et al., Plant Cell Physiol., 27:1593, 1986). Hence, it is believed that the Δ9 desaturases of Anabaena and Synechocystis have an activity of reacting with the substrate 18:0/16:0-molecular species to desaturate the 18:0 at the position of sn-1 into 18:1 Δ9, whereas the Δ9 desaturase of Anacystis has an activity of reacting with the substrate 16:0/16:0-molecular species to desaturate the 16:0 at the position of sn-1 into 16:1 Δ9. Considering the fact that higher plants contain a larger amount of 16:0/16:0-saturated molecular species, the Anacystis-type Δ9 desaturase is more suitable than the Anabaena- and Synechocystis-type enzymes for the purpose of desaturating saturated molecular species in higher plants.

As will be shown below in the Examples, the genes of the present invention include genes encoding Δ9 desaturase which contains the amino acid sequence substantially shown in SEQ ID NO: 4 and their degenerate isomers capable of encoding the same polypeptide except for degenerate codons. The genes of the present invention are predominantly in the form of DNA chains. The "amino acid sequence substantially shown in SEQ ID NO: 4" includes not only the amino acid sequence shown in SEQ ID NO: 4 but also those amino acid sequences in which part of the amino acid sequence of SEQ ID NO: 4 may be modified by deletions, substitutions and/or additions, provided that a Δ9 desaturase activity is retained.

The genes of the present invention can be prepared by any conventional known techniques from the aforementioned blue-green algal cells.

In brief, the genes of the present invention can be prepared by culturing blue-green algal cells, collecting them, preparing genomic DNA from the blue-green algal cells by a conventional known technique such as ethanol precipitation or the like, preparing a gene library based on the genomic DNA, selecting clones containing the desired gene from the library and amplifying the clone DNA.

Vectors to be used for the preparation of the gene library include any conventional vectors and specific examples include phages such as λ DASH II (Stratagene), cosmids such as pWE15 (Stratagene), phagemids such as pBluescript II (Stratagene) and the like. The genes of the present invention can be introduced into these vectors by a conventional known method selected for a specific kind of vectors.

Clones in which the gene of the present invention has been introduced is selected from the thus prepared gene library.

The methods for clone selection include any conventional known selection methods, for example, immunological methods such as plaque hybridization and colony hybridization in which antibodies are used, as well as plaque hybridization and colony hybridization in which nucleotide probes are used. A preferred criterion for the nucleotide probe selection is to use as a probe part of base sequences which are estimated to be similar to the genes of the present invention (eg., base sequences encoding part of the 260–295 amino acid sequence of MSCD2 in FIG. 1).

The base sequence of the gene of the present invention in the selected clone can be determined and confirmed by any conventional known methods such as the Maxam-Gilbert method (Maxam-Gilbert, Methods Enzymol., 65:499, 1980), the dideoxynucleotide chain terminator technique using M13 phage (Messing, J. et al., Gene, 19:269, 1982) and the like.

The actual expression of Δ9 desaturase can be confirmed by, for example, the method of Wada et al. (J. Bacteriol., 175:6056, 1993).

Once the genes of the present invention are sequenced, they can be synthesized by any conventional known methods such as a phosphite method using a commercially available DNA synthesizer.

The gene of the present invention or a polynucleotide that contains part of the gene and which has the Δ9 desaturase activity is separated from the selected clones, incorporated into a vector for gene introduction into a plant host, introducing the vector into a plant cell and expressing Δ9 desaturase in the plant, thereby imparting a chilling resistance to the plant.

The kind of plants into which the genes can be introduced is not particularly limited.

The vectors for gene introduction should be constructed such that the Δ9 desaturase gene can be expressed stably in plants. More specifically, a promoter, a DNA chain encoding a translation control region, a DNA chain encoding a peptide for transfer into chloroplasts, the gene of the present invention or a polynucleotide that contains part of the gene and which has the Δ9 desaturase activity, a DNA chain encoding a termination codon and a terminator should be incorporated in appropriate positions. As construction elements for the introduction of genes other than the gene of the present invention, any conventional known elements can be used. Preferred examples of the DNA chain encoding a peptide for transfer into chloroplasts include a gene for the small subunit of pea ribulose-1,5-bisphosphate carboxylase. Examples of the promoter include a cauliflower mosaic viral 35S promoter. Examples of the terminator include a terminator of nopaline synthase.

The methods for gene introduction into plant cells include any conventional known methods such as the methods described in "Plant genetic transformation and gene expression; a laboratory manual", Draper, J. et al. eds., Blackwell Scientific Publications, 1988. Exemplary methods include biological methods using viruses and Agrobacterium, physicochemical methods such as electroporation, a polyethylene glycol method and microinjection, and the like. Among these, the use of Agrobacterium is preferred for dicotyledonous plants such as tobacco since it secures stable transformation. The methods using Agrobacterium include an intermediate vector method using a wild-type tumor plasmid (Nature, 287 (1980) p.654; Cell, 32 (1983) p.1033; EMBO J., 3 (1984) p.1525), an intermediate vector method using a vector deficient of a tumor formation gene region on T-DNA (EMBO J., 2 (1983) p.2143; Bio/Technology, 3(1985) p.629), a binary vector method (Bio/Technology, 1 (1983) p. 262; Nature, 303 (1983) p. 179; Nucl. Acids Res., 12 (1984) p.8711) and the like. Any of these methods can be used. Examples of the methods in which plants are infected with Agrobacterium include direct inoculation to cultured cells, protoplast co-cultivation, a leaf-disk method and the like. A leaf-disk method is preferred in terms of the ability to produce a large number of transformed plants in a direct and easy way.

In order to regenerate plants, the transformed plant cells may be cultured in known media such as Murashige-Skoog medium that are supplemented with selection antibiotics, plant growth hormones and any other agents. The rooted seedlings are transplanted into the soil and cultured for growth to complete plants.

The transformed plants which have been grown to mature plants can be tested for chilling resistance by the following procedure:

A test plant is cultured at a temperature (eg., 25° C.) at which it does not receive a low temperature injury and then cultured temporarily (eg., for a week) at a low temperature (eg., 4° C.). The injury to the plant, for example, chlorosis and the reduction of fertility are measured. Alternatively, the amount of the plant growth may be compared with that of a control plant.

The present invention will now be explained in greater detail with reference to the following examples which are by no means intended to limit the scope of the present invention.

EXAMPLE 1

The Cloning of a DNA Fragment of Open Reading Frame Flanking at the Upstream Side of the Δ12 Desaturase Gene (des A) of *Anabaena variabilis*

*Anabaena variabilis* IAM M-3 provided by Institute of Molecular and Cellular Biosciences, University of Tokyo, was cultured in about 100 ml of a BG-11 medium ("Plant Molecular Biology", Shaw, C. H. ed., p.279, IRL PRESS, 1988). The culture was shaken at 25° C. under 1,000-lux fluorescent light with a 120-rpm shaking rate to grow bacteria thoroughly. The culture solution was centrifuged at room temperature at 5,000 g for 10 minutes to collect the precipitated cells.

For the purpose of preparation of genomic DNA, the cells were suspended in 50 ml of solution A (50 mM Tris-HCl, 1 mM EDTA, pH 8.0), washed and centrifuged to collect the precipitated cells. Subsequently, the resulting cells were suspended in 15 ml of solution B (50 mM Tris-HCl, 20 mM EDTA, 50 mM NaCl, 0.25 M sucrose, pH 8.0). To the suspension, 40 mg of lysozyme (Sigma) dissolved in solution B was added and the mixture was shaken at 37° C. for 1 hour. To the shaken culture, proteinase K (15 mg) and SDS (final concentration of 1%) were added and the mixture was shaken at 37° C. overnight. To the shaken culture, $NaClO_4$ was added to a final concentration of 1M and 20 ml of chloroform/isoamyl alcohol (24:1) was also added. The resulting mixture was shaken for 10 minutes and then centrifuged to collect the aqueous layer. After re-extraction with chloroform/isoamyl alcohol (24:1), 50 ml of ethanol was added to the aqueous layer and a genomic DNA preparation was collected by winding the DNA on a glass rod. The DNA preparation was dissolved in 20 ml of solution A and NaCl was added at a final concentration of 0.1 M. RNase was added at a final concentration of 50 mg/ml and the resulting mixture was incubated at 37° C. for 1 hour. Subsequently, extraction with an equal amount of phenol saturated with solution A was performed twice and ethanol was then added to the aqueous layer, thereby collecting the precipitated genomic DNA. The genomic DNA was washed with 70% ethanol and dissolved in 1 ml of solution A to prepare an *Anabaena variabilis* genomic DNA solution.

Sakamoto et al., reporting the presence of an open reading frame (ORF) flanking at the upstream side of Δ12 desaturase gene, suggested that it may have something to do with the desaturase when they made a speech on the cloning of a membrane lipid-bound fatty acid Δ12 desaturase gene derived from *Anabaena variabilis* (Lecture Abstract No. 3aF04 in the 1993 annual meeting of The Japanese Society of Plant Physiologists). However, the function of the ORF was not identified. The inventors took interest in the ORF and its function. Thus, they synthesized four primers (SEQ ID NOs: 5–8) giving attention to three base sequences in the DNA chain of the ORF and used the primers in PCR with *Anabaena variabilis* genomic DNA used as a template.

Of the four primers, those having the base sequences of SEQ ID NOs: 5 and 6 encode sense strands and those having the base sequences of SEQ ID NOs: 7 and 8 encode antisense strands. The base sequences of SEQ ID NOs: 6 and 7 are derived from the same amino acid sequence. A primer set was selected from each of the sense and antisense strands and PCR was performed with 4 combinations of primers in total. The primers (20 $\mu$M, each) and the *Anabaena variabilis* genomic DNA (1 $\mu$g) were added to the reaction solution (100 $\mu$l) and reaction was performed with a GeneAmp PCR Kit (TAKARA SHUZO CO., LTD.). The PCR was performed through 35 cycles, each cycle consisting of 95° C. (1 minute), 45° C. (1 minute) and 72° C. (2 minutes). In the first cycle, the temperature of 95° C. was maintained for 3 minutes. After the end of the reaction, the reaction solution (10 $\mu$l) was electrophoresed on a 2% agarose gel to separate the synthesized DNA for analysis. As a result of the analysis, a DNA fragment having an expected size (about 190 bp) was detected as a main band in the DNAs synthesized using a combination of primers having the base sequences of SEQ ID NOs: 6 and 8. The DNA fragment (hereinafter referred to as "des 9 var") was treated with a Klenow fragment to make blunt ends and then cloned into plasmid pTZ18R (Pharmacia) at a SmaI site, followed by determination of the base sequence with a fluorescent DNA sequencer (Applied Biosystems). The determined base sequence is shown in SEQ ID NO: 1. The amino acid sequence (SEQ ID NO: 2) deduced from this base sequence had a significant homology with mouse stearoyl-CoA desaturase (see FIG. 1 showing the amino acid sequence encoded by the des 9 var fragment as compared with that of mouse stearoyl-CoA desaturase (MSCD2)).

Subsequently, *Anacystis nidulans* genomic DNA was analyzed by Southern blotting technique with the des 9 var fragment used as a probe. Restriction enzymes XhoI, PstI and BamHI were used individually to cleave *Anacystis nidulans* genomic DNA (about 0.1 $\mu$g). The resulting DNA fragments were separated by electrophoresis on a 0.8% agarose gel and then blotted on a nylon membrane (Hybond-$N^+$; Amersham). Probe DNAs were labelled with [$\alpha$-$^{32}$P] dCTP using a Multiprime DNA labelling Kit (Amersham). The probe DNAs were reacted with the membrane by incubation in a solution consisting of a 6×SSPE [1×SSPE was a mixture of a 10 mM phosphate buffer (pH 7.0), 1 mM EDTA and 0.15 M NaCl], 0.2% SDS and 100 $\mu$g/ml herring sperm DNA at 55° C. for 16 hours. The resulting membrane was then washed by shaking it twice in 2×SSC [1×SSC was a mixture of 0.15 M NaCl and 15 mM sodium citrate] at room temperature for 15 minutes and twice in 0.1×SSC at 40° C. for 15 minutes and analyzed by autoradiography. As a result, only one DNA fragment was detected in the case where the genomic DNA had been cleaved with any of the restriction enzymes (see FIG. 2. In FIG. 2, "Non" means that the genomic DNA was not cleaved with any restriction enzymes.).

EXAMPLE 2

Figure 3:
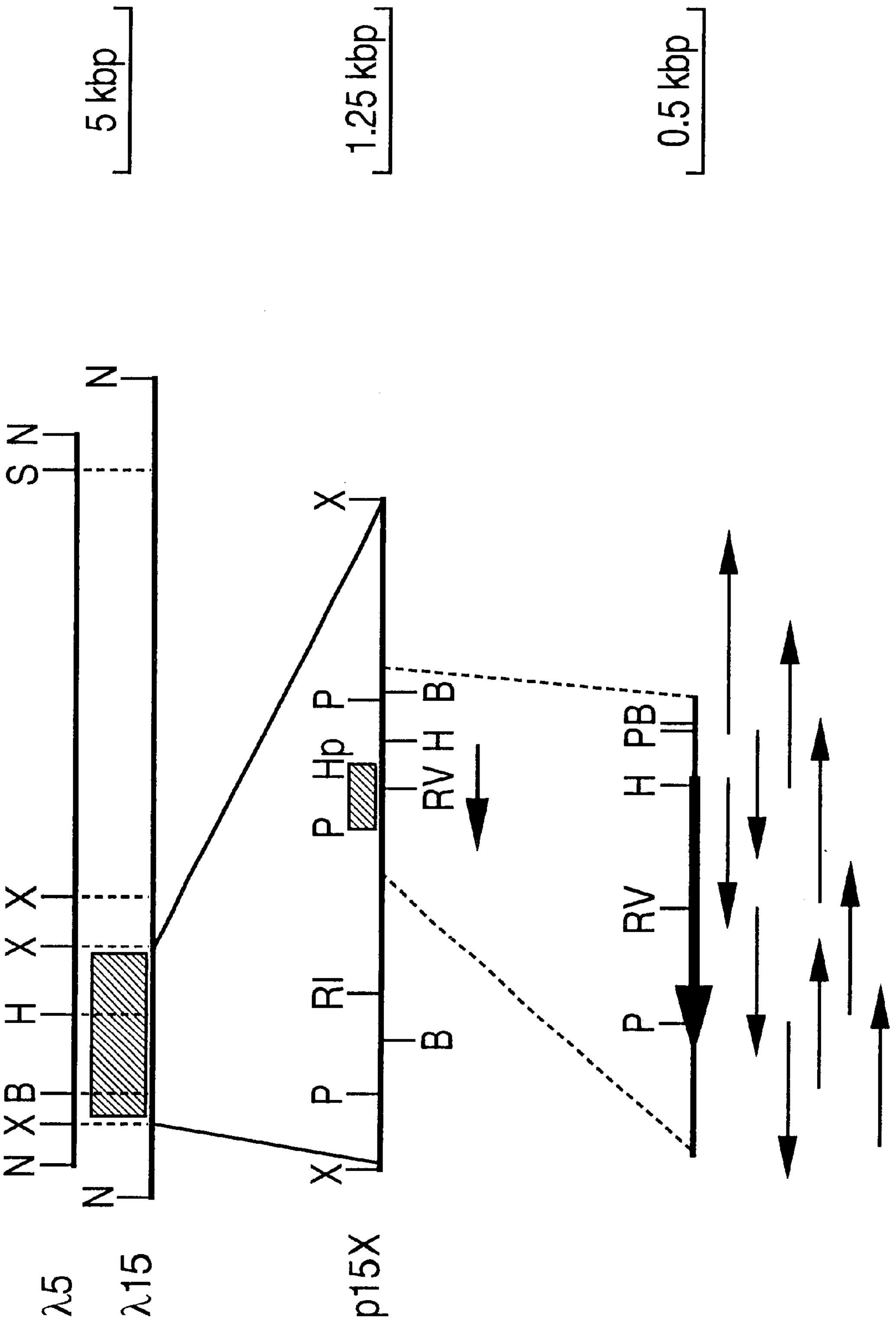
FIG. 3 shows the relationship among inserted DNA fragments, λ5, λ15 and p15X. Thick arrows show the positions in which a protein is encoded and their directions. Thin arrows show the positions which were sequenced and their directions.
Figure 5:
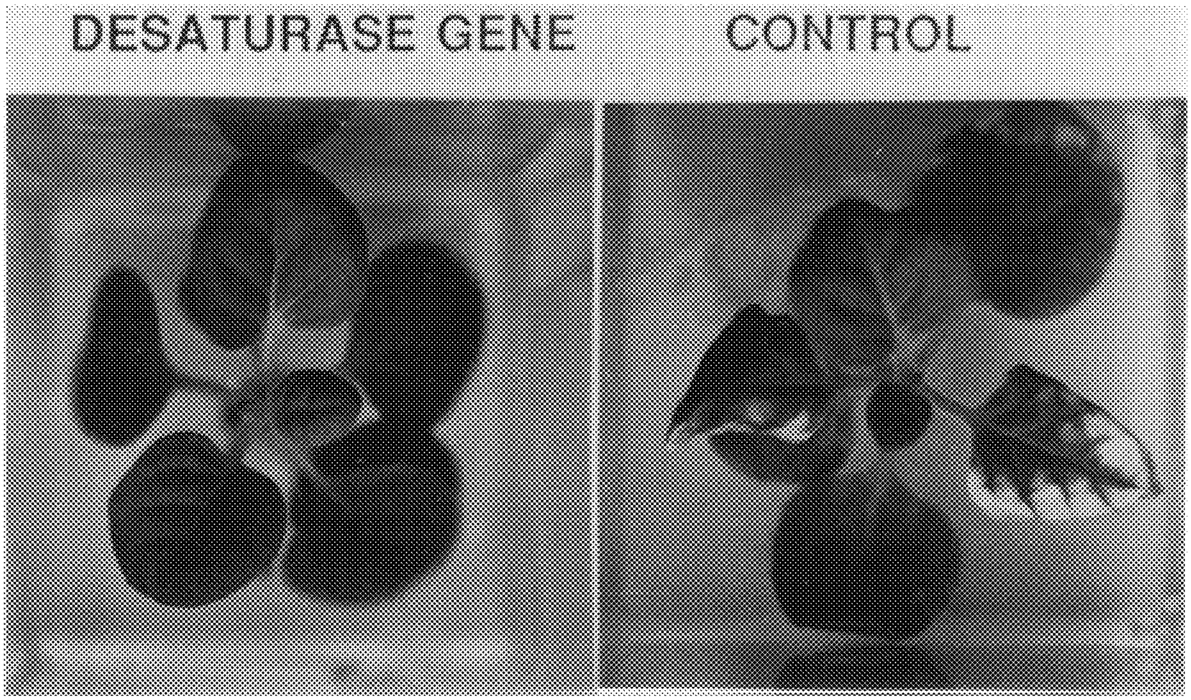
FIG. 5 is a pair of photographs showing in biological morphology the influence of a low temperature treatment on transformed tobacco plants. The left photo shows the result of the low temperature treatment of tobacco transformed with a desaturase gene and the right photo shows the result of the low temperature treatment of tobacco transformed with pBI121.

Cloning of a DNA Chain in *Anacystis nidulans* Genomic DNA Having High Homology With the des 9 var Fragment The cultivation of *Anacystis nidulans* R2-SPc provided by Institute of Molecular and Cellular Biosciences, University of Tokyo and the preparation of genomic DNA were conducted by the same method as in the case of *Anabaena variabilis*. The genomic DNA (about 100 $\mu$g) was partially digested with Sau3AI and DNA fragments of about 9–23 kbp were then collected by ultracentrifugation in a sucrose density gradient according to the method described in "Molecular Cloning, 2nd edition, pp.2.85–2.87 (Sambrook, J. et al., eds., Cold Spring Harbor Laboratory, 1989). The collected DNA fragments were cloned into lambda phage vector λ DASH II (Stratagene) cleaved with BamHI and HindIII and then packaged in phage particles to yield an *Anacystis nidulans* genomic DNA library. *E. coli* P2392 cells were infected with the phage library and cultivated in NZYM-agar plates of about 15 cm in diameter. A total of about 100,000 plaques were formed and then blotted on nylon membranes (Hybond-$N^+$; Amersham). In the same manner as in the above Southern analysis, the des 9 var fragment labelled with [$\alpha$-$^{32}$P]dCTP was reacted with the resulting membranes and positive phages detected by autoradiography were screened to yield about 30 phage clones having different signal intensities, from which 12 clones were selected. Phage DNA was obtained from each clone by a conventional method. The obtained phage DNA was cleaved with several kinds of restriction enzymes and separated by electrophoresis on a 0.8% agarose gel, followed by blotting on a nylon membrane. The resulting membrane was analyzed by Southern blotting technique under the same conditions as in the above screening and comparison was made on the lengths and signal intensities of DNA fragments hybridizing with the probe DNAs. As a result, 2 clones, λ5 and λ15, showed the strongest signals. Since these two clones had inserts DNA of 11 and 15 kbp, it was estimated that they were sufficiently long to contain the entire region of the desired ORF. The insert DNA of each of the two clone was cleaved with several restriction enzymes and analysed by Southern blotting technique. As a result, a DNA fragment of about 5 kbp was detected in both clones when they were cleaved with XhoI and hybridized. This DNA fragment was subcloned into pBluescript SK-(Stratagene) at a XhoI site to yield plasmids p5X and p15X which contained the DNA fragments derived from λ5 and λ15, respectively. The detailed restriction maps of p5X and p15X were prepared and compared. These maps show that both p5X and p15X contain the same genomic DNA fragment (see FIG. 3 showing the correlativity between the DNA inserts of λ5 and λ15. The hatched rectangles show DNA fragments hybridizing with the probe des 9 var fragment in the process of screening. Thick arrows show the region of des 9 nid (to be described below) and the direction of a sense strand. Thin arrows show the sequencing direction of a region containing des 9 nid. The bars of 5 kbp, 1.25 kbp and 0.5 kbp show size markers for the left maps. Abbreviations of restriction enzymes have the following meanings: B, BamHI; H, HindIII; N, NotI; Hp, HpaI; RI, EcoRI; RV, EcoRV; S, SalI; P, PstI; and X, XhoI).

Deletion plasmids were prepared from p15X with restriction enzymes or ExoIII and the base sequence of a DNA fragment of about 2 kbp which contained a region hybridizing with the des 9 var fragment was determined with a fluorescent DNA sequencer (see FIG. 3). As a result, it was estimated that the DNA fragment would contain ORF (des 9 nid) of 834 bp (SEQ ID NO: 3) which would encode 278 amino acids (SEQ ID NO: 4). The amino acid sequence had about 80% homology with the amino acid sequence (SEQ ID NO: 2) of the previously cloned des 9 var fragment derived from *Anabaena variabilis*. A search for highly homologous amino acid sequences was conducted with nucleic acid and amino acid sequence analysis software GENETYX (Software Development) and nucleic acid and amino acid sequence data bases EMBL and DDBJ. The results of the search revealed that des 9 nid had about 30% general homology with mouse stearoyl-CoA desaturase but that part of des 9 nid had a very high homology with the mouse desaturase (see FIG. 4 showing the amino acid sequence of des 9 nid as compared with that of mouse stearoyl-CoA desaturase (MSCD2)), suggesting that the obtained des 9 nid should encode an enzyme capable of desaturating fatty acids.

EXAMPLE 3

Determination of Activity by the Expression of the des 9 nid Gene in *E. coli*

*Anacystis nidulans* desaturase has only a Δ9 desaturase activity or the ability to desaturate lipid-bound saturated fatty acids at the 9 position (Bishop, D. G. et al., Plant Cell Physiol., 27:1593, 1986). For this reason, an attempt was made to express the polypeptide encoded by des 9 nid in *E. coli* and measure its activity.

Since direct expression from p15X is difficult, a vector for expression in *E. coli* was prepared. Specifically, pET3a (Novagen) was selected as a vector and des 9 nid was cloned into pET3a between the sites of NdeI and BamHI such that extra amino acids would not be added to the amino terminus of the polypeptide encoded by des 9 nid by the following procedure:

In order to insert a BamHI site just downstream of the C terminus of the des 9 nid-encoded protein, PCR was performed with the base sequences of two parts having the C terminus therebetween. Specifically, the PCR was performed with the following two primers and using p15X as a template to yield a product of about 140 bp.

Sense primer:5'-ACGTCATGGCCTGCAGT (a PstI site is underlined) (SEQ ID NO:9)

Antisense primer:5'-CGCGGATCC TTAGTTGTTTGGAGACG (a single line is drawn under a BamHI site and a double line is drawn under a stop codon) (SEQ ID NO: 10)

The product was subcloned into pUC19 at a SmaI site and the accuracy of the base sequence was confirmed. As a result, an EcoRI site was created downstream of the BamHI site in the resulting plasmid. The plasmid was cleaved sequentially with EcoRI and PstI. In the meantime, p15X was cleaved with the same restriction enzymes to introduce a BamHI site just downstream of the stop codon. The plasmid was cleaved with SalI and a fill-in reaction was then performed with a DNA polymerase Klenow fragment in the presence of four kinds of dNTP, followed by cleavage with HindIII. The adaptor consisting of the following two synthesized DNAs was inserted into the resulting plasmid, thereby introducing an NdeI site into the amino terminus. The adaptor was a mixture of equal molar amounts of the following two DNAs.

5'-CATATGACCCTTGCTATCCGACCCA (an NdeI site is underlined) (SEQ ID NO: 11) and

5'-AGCTTGGGTCGGATAGCAAGGGTCATATG (a single line is drawn under an NdeI site and a double line is drawn under part of a HindIII site) (SEQ ID NO: 12)

The resulting plasmid (pDes9Nde) was introduced into competent cells of *E. coli* strain BL21 (DE3) (Novagen) which were prepared by a conventional method (Molecular cloning, pp.250–251, 1982). Transformed strain BLDES1 was obtained by selection for ampicillin resistance.

The BLDES1 strain and pET3a-containing BL21 strain (BL1) were inoculated in a 100-ml M9 medium (containing 200 μg/ml ampicillin, 4 mg/ml glucose, 10 μM $FeCl_3$, 0.5 μg/ml vitamin B1, 1 mg/ml casamino acids) and cultured at 37° C. The cultivation was continued until the turbidity of the culture solution reached 0.5 O.D. at a wavelength of 600 nm. Isopropylthiogalactoside (IPTG) was added at a final concentration of 1 mM to the culture solution. The cells were cultured for an additional 1 hour to induce the expression of the Δ9 desaturase gene. The *E. coli* pellets were collected and washed with 1.2% NaCl, followed by lipid extraction. Lipids were extracted by the method of Bligh and Dyer (Can J. Biochem. Physiol., 37:911, 1959) and reacted with 5% methanolic hydrochloride (2.5 ml) at 85° C. for 2.5 hours under a completely sealed condition to yield methylated fatty acids. The produced fatty acid methyl esters were extracted 4 times with hexane (2.5 ml) and concentrated by removing the solvent with nitrogen gas. The fatty acid methyl esters were analyzed by gas chromatography. The fatty acids were identified by comparison of retention times with standard fatty acid methyl esters. The quantitative analysis was conducted with a Chromatopack C-R7A plus (Shimadzu Corp.). The results are shown in the following Table 1.

TABLE 1

Fatty Acid Composition in *E. coli*

| Strain | 16:0 | 16:1 | 18:1 Δ 11 | Others |
|---|---|---|---|---|
| BL1 (0 hour) | 47 | 20 | 29 | 4 |
| BL1 (1 hour) | 50 | 17 | 29 | 4 |
| BLDES1 (0 hour) | 44 | 22 | 30 | 4 |
| BLDES1 (1 hour) | 40 | 28 | 28 | 4 |

The hours indicate the time of protein induction with IPTG.

The results revealed that 16:1 increased in the BLDES1 strain, showing that the gene of the present invention has an activity of desaturating 16:0.

The two strains were cultured in an M9 medium supplemented with 0.1 mM stearic acid and a comparison was made in the same manner as above. In contrast to the BL strain, the BLDES1 strain produced not only 16:1 but also 18:1 Δ9. This indicates that the polypeptide encoded by des 9 nid can use not only 16:0 but also 18:0 as a substrate to produce unsaturated fatty acids.

EXAMPLE 4

Introduction of the des 9 nid Gene Into Tobacco Plants

The *Anacystis nidulans*-derived des 9 nid gene was incorporated into tobacco plants as follows:

(1) Construction of Vector Plasmid for Expression in Plants

Plasmid pDes9Nde was cleaved with SacI and SalI to yield a des 9 nid gene fragment held between the sites of the two restriction enzymes. A chloroplast-transit sequence was cut off from the clone pSNIP9 containing a pea RuBisCO gene (Schreicher et al., EMBO J. 4, 25 (1985)) with HindIII and SphI and cloned into pUC118 cleaved with the same restriction enzymes, thereby yielding plasmid pTRA3 containing a multi-cloning site downstream of the transit sequence. The HindIII site of this plasmid was cleaved and filled in with a Klenow enzyme, followed by insertion of a XbaI linker (pTRA3X). The plasmid pTRA3X was cleaved with SalI and SacI and the des 9 nid fragment which had been obtained by cleavage with the same restriction enzymes was inserted (pTRA3Xdes9). In the pTRA3Xdes9, the des 9 nid gene would be translated, following the transit sequence of RuBisCO, in the same reading frame. This plasmid was cleaved with SacI and XbaI and inserted into the following vector for plants. Plant expression-type binary plasmid pBI121 (Clonetech) was cleaved with SacI and XbaI to yield β-glucuronidase gene (GUS gene)-free plasmid pBI(-GUS). The transgene prepared above was inserted into the plasmid pBI(-GUS) between the cauliflower mosaic viral 35S promoter and the nopaline synthase (NOS) terminator to yield a vector (pBI121(-GUS)Rbsc-des9) for introduction into plants.

(2) Introduction of pBI121(-GUS)Rbsc-des9 Into Agrobacterium

*Agrobacterium tumefaciens* LBA4404 (Clonetech) was inoculated in a 50-ml YEB medium (5 g beef extract, 1 g yeast extract, 1 g peptone and 5 g sucrose per liter supplemented with 2 mM $MgSO_4$ (pH 7.4)) and cultured at 28° C. for 24 hours. The cultured solution was centrifuged at 3,000 rpm at 4° C. for 20 minutes to collect the cells. The cells were washed 3 times with 10 ml of 1 mM Hepes-KOH (pH 7.4) and once with 3 ml of 10% glycerol. The cells were suspended in 3 ml of 10% glycerol to prepare Agrobacterium cells for DNA introduction.

The thus obtained cell solution (50 μl) and the plasmid pBI121(-GUS)Rbsc-des9 (1 μg) were placed in a cuvette and treated with electric pulses using an electroporation apparatus Gene Pulser (BioRad) under the conditions of 25 μf, 2500 V and 200Ω, thereby introducing the plasmid DNA into the Agrobacterium. The cell solution was transferred into an Eppendorf tube and 800 μl of an SOC medium (20 g tryptone, 5 g yeast extract, and 0.5 g NaCl per liter supplemented with 2.5 mM KCl, 10 mM $MgSO_4$, 10 mM $MgCl_2$ and 20 mM glucose (pH 7.0)) was added. The cells were cultured statically at 28° C. for 1.5 hours. The culture solution (50 μl) was inoculated in a YEB agar medium (agar 1.2%) supplemented with 100 ppm kanamycin and cultured at 28° C. for 2 days.

Well separated colonies were selected from the resulting colonies and plasmid DNA was prepared from the selected colonies by an alkaline method. The plasmid DNA was digested with appropriate restriction enzymes. The resulting DNA fragments were then separated by electrophoresis on a 1% agarose gel and analyzed by Southern blotting technique using $^{32}P$-labelled des 9 nid gene fragment as a probe; it was confirmed that the Agrobacterium cells contained the plasmid pBI121(-GUS)Rbsc-des9. This *Agrobacterium tumefaciens* cell line is abbreviated as "ALBBSDES".

(3) Transformation of Tobacco

The cell line ALBBSDES was cultured with shaking in an LB liquid medium supplemented with 50 ppm kanamycin at 28° C. for 2 hours. The culture solution (1.5 ml) was centrifuged at 10,000 rpm for 3 minutes to collect the cells. The cells were then wash with a 1-ml LB medium to remove kanamycin. Additionally, the cell solution was centrifuged at 10,000 rpm for 3 minutes to collect the cells. The cells were then re-suspended in a 1.5-ml LB medium to prepare a cell solution for infection.

For infection of tobacco, a young leaf of tobacco was taken and immersed into a 0.5% sodium hypochlorite solution in water for 10 minutes. Subsequently, the leaf was washed 3 times with sterilized water and wiped with sterilized filter paper to prepare a leaf sample to be infected. The leaf was cut off aseptically with a knife in pieces of 1 $cm^2$ each. The pieces were placed on the solution of Agrobacterium such that the back of each piece faced up and shaken gently for 2 minutes. The pieces were then placed on sterilized filter paper to remove excess Agrobacterium. Whatman No.1 filter paper (ϕ 7.0 cm) was placed on an MS-B5 medium (containing 1.0 ppm benzyladenine, 0.1 ppm naphthaleneacetic acid, and 0.8% agar) (Murashige, T. and Skoog, F. Plant Physiol., 15:473, (1962)) in a plate and each piece of the sample leaves was placed on the filter paper such that the back of the leaf faced up. The plate was sealed with a parafilm and the leaf was cultured through cycles of 16 hours under light and 8 hours in the dark at 25° C. for 2 days. Subsequently, the leaf was transferred into an MS-B5 medium supplemented with 250 ppm calforan and cultured under the same conditions to remove the Agrobacterium. Additionally, the leaf was placed in an MS-B5 medium supplemented with 250 ppm calforan and 100 ppm kanamycin on the bottom of a plate and cultured under the same conditions for 7 days. In the mean time, the calluses were formed around the leaf and shoots were initiated. After cultivation for an additional 10 days, the extended shoot was placed in an MS-HF medium (MS-B5 medium free from benzyladenine and naphthaleneacetic acid) supplemented with 250 ppm calforan and 100 ppm kanamycin. After cultivation for 10 days, the rooted shoot was selected as a kanamycin-tolerant transformant and transplanted into an MS-HF medium supplemented with 250 ppm calforan in a plant box.

EXAMPLE 5

Southern and Northern Analyses of the Transformed Tobacco Genome

DNA was extracted from the kanamycin-tolerant tobacco and analyzed by the Southern and Northern blotting techniques to confirm the introduction and the expression of the desired gene. The extraction of the genomic DNA was conducted by a CTAB method according to a manual (Rogers, S. O. & Bendich, A. J.: Plant Molecular Biology Manual A6; 1 (1988)). In brief, tobacco leaves (2 g) were ground in liquid nitrogen and genomic DNA was extracted with a CTAB extraction buffer. The DNA (10 μg) was cleaved with EcoRI and XbaI and then electrophoresed on a 0.7% agarose gel, followed by blotting of the separated DNA fragments with 0.4 N NaOH on a nylon membrane (Hybond N+; Amersham). The transit-containing desaturase gene derived from pTRA3Xdes9 was used as a probe for hybridization with the membrane at 65° C. for 16 hours, thereby confirming that the desired gene was introduced into the tobacco genome.

RNA was extracted from the tobacco leaves (about 2 g) and analyzed to confirm the expression of the transgene. The procedure consisted of extracting poly(A)+RNA with guanidium thiocyanic acid (Nagy, F. et al., Plant Molecular Biology Manual B4; 1 (1988)) and electrophoresing on a formaldehyde-containing agarose gel. The RNA was blotted on a nylon membrane (Hybond N; Amersham) and analyzed under the same hybridization condition as in the Southern method. Among the transformants expressing various amounts of RNA, those expressing large amounts of RNA were selected and analyzed for fatty acids.

EXAMPLE 6

Fatty Acid Analysis of the Lipids in the Transformed Tobacco Plants

Lipids such as phosphatidylglycerol (PG) and sulfoquinovosyldiacylglycerol (SQDG) were prepared by the following method from the leaves of the transformed tobacco plants which were verified for high RNA expression in Example 5 and those of control tobacco plants transformed with pBI121. Their fatty acid compositions were analyzed. The root lipids were also analyzed in regard to part of the transformants and non-transformants.

(1) Extraction of Total Lipids

Lipids were extracted by the Bligh-Dyer method (Can J. Biochem. Physiol., 37:911, 1959). Two grams by wet weight of the leaves (1 g, when part of the root was used as a sample) were sliced with a knife and 20 ml of chloroform/methanol (1:2, volume ratio) was added. The leaves were disrupted with a homogenizer and left to stand for 15 minutes. Chloroform (12 ml) and distilled water (12 ml) were added to the disrupted leaves and the mixture was stirred vigorously. The mixture was centrifuged at 3,000 rpm at 4° C. for 30 minutes to separate the aqueous and organic layers. The organic (low) layer was collected and an appropriate amount of ethanol was added. The solvents were distilled off at 30° C. under a reduced pressure with a rotary evaporator. The residue was dissolved in 2 ml of chloroform/methanol (1:4, volume ratio) to prepare a total lipid extract. Part of the total lipid extract was treated with 5% methanolic hydrochloric acid by the following method to yield methylated fatty acids.

(2) Fractionation of Lipids

A suspension (2.5 ml) of DEAE-Toyopearl 650C (TOSOH) was mixed with 25 ml of a 1 M sodium acetate solution in water (pH 7.0) to prepare an acetic acid form. The resulting suspension was washed sequentially with distilled water and methanol and suspended in methanol. The resulting suspension was packed in a column (i.d. 2 cm) to 1.5 cm in height and washed with 50 ml of chloroform/methanol (1:4, volume ratio).

Subsequently, the total lipid extract was applied to the column. Monogalactosyldiacylglycerol (MGDG), digalactosyldiacylglycerol (DGDG), phosphatidylethanolamine (PE) and phosphatidylcholine (PC) were eluted with 50 ml of chloroform/methanol (1:4, volume ratio) to prepare neutral lipid (MGDG, DGDG, PE and PC) fractions. Then, phosphatidylserine (PS) was eluted out with 5 ml of acetic acid and the acetic acid was washed away with 20 ml of chloroform/methanol (1:4, volume ratio). A fraction containing PG, SQDG and phosphatidylinositol (PI) was obtained by extraction with 50 ml of an aqueous solution of chloroform, methanol and 10 M ammonium acetate (20:80:0.2, volume ratio). Ethanol (15 ml) was added to this fraction and the solvents were distilled off under a reduced pressure. The residue was dissolved in 0.2 ml of chloroform/methanol (2:1, volume ratio) to prepare acidic lipid (PG, SQDG and PI) fractions.

The MGDG, DGDG, PE and PC fractions were further fractionated by silicic acid column chromatography (Iatrobeads, Iatoron Laboratories Inc.). More specifically, the samples dissolved in chloroform (1 ml) were applied to a column equilibrated with chloroform and eluted sequentially with chloroform/acetone (4:1), acetone and methanol, whereby glycolipids (MGDG and DGDG) were eluted with acetone and phospholipids (PC and PE) with methanol.

(3) Isolation and Purification of PG by Thin Layer Chromatography (TLC) and Fatty Acid Analysis The fractions obtained in step (2) were separated with a silica gel-TLC plate #5721 (Merck). As developing solvents, chloroform/acetone/methanol/acetic acid/water (50:20:10:15:5, volume ratio) was used for the separation of acidic lipids and chloroform/methanol/water (70:21:3, volume ratio) was used for the separation of neutral lipids. After separation by TLC, primulin (80% solution in acetone) was sprayed to develop fluorescence under ultraviolet light. The various classes of the lipid fractions were estimated by comparison of mobility with standard lipids. The fluorescence-developing lipids were scraped together with the silica gel and placed in test tubes equipped with screw caps. When the fatty acid compositions of the lipids were to be estimated, 3 ml of methanolic 5% hydrochloric acid was added to the lipids and the mixtures were reacted at 85° C. for 2 hours under a completely sealed condition to yield methylated fatty acids. In the meantime, in order to determine the fatty acid compositions at the sn-1 and sn-2, the lipids were collected from the scraped silica gel with 5 ml of a chloroform/methanol (2:1) mixed solution and dried. To the lipids, 1 ml of 50 mM TrisCl (pH 7.2) and 0.05% Triton X-100 were added and the mixture was stirred vigorously to disperse the lipids. *Rhizopus delemar*-derived lipase (2500U; Boehringer) was added to the dispersion and the mixture was held at 37° C. for 30 minutes to liberate fatty acids selectively at the sn-1 position. After the reaction products were concentrated, unreacted lipids, Lysolipids and free fatty acids were separated by TLC using chloroform/acetone/methanol/acetic acid/water (10:4:2:3:1) as a developing solvent. These substances were collected from the gel and reacted with methanolic hydrochloric acid by the same method as described above to yield methylated fatty acids. The produced fatty acid methyl esters were extracted 4 times with 3 ml of hexane and concentrated by distilling off the solvent under a reduced pressure. The fatty acid methyl esters were analyzed by gas chromatography. The fatty acids were identified by comparison of retention time with standard fatty acid methyl esters. The quantitative analysis was conducted with a Chromatopack C-R7A plus (Shimadzu Corp.). The results for the total lipids, PG and other representative lipids are shown in Tables 2, 3 and 4, respectively. These tables show average analytical values for 2 controls, and 2 or 3 independent transformants.

In regard to the other lipids, MGDG, DGDG, SQDG, PC, PE and PC, it is clear that 16:0 decreased with a corresponding increase of about 10% in 16:1 and that the desaturation of 18:0 was enhanced. In MGDG and DGDG, 16:1 was produced mainly at the sn-1 position but the production of a small amount of 16:1 was also detected at the sn-2 position. It was found that the desaturation of MGDG, DGDG, SQDG and PG, which were lipids present predominantly in chloroplasts, was surprisingly enhanced by expressing the desaturase of the blue-green alga *Anacystis nidulans* in the chloroplasts of higher plants. There was a high possibility that these four kinds of lipids which were present in the membranes of *Anacystis nidulans* could be used as substrates for the desaturase. It was quite surprising that palimitic acid and stearic acid were desaturated in PC, PE and PI because these lipid are absent in the membranes of *Anacystis nidulans* but present predominantly outside the chloroplasts in higher plants.

TABLE 2

Results of fatty acid analysis on the total lipids in leaves

| Plant | 16:0 | 16:1 | 16:2 | 16:3 | 18:0 | 18:1 | 18:2 | 18:3 | Σ 16:0 + 18:0 |
|---|---|---|---|---|---|---|---|---|---|
| Control plant | 17 | 3 | 1 | 4 | 3 | 1 | 9 | 63 | 20 |
| Transformed plant | 10 | 12 | 1 | 5 | 1 | 2 | 14 | 56 | 11 |

TABLE 3

Results of fatty acid analysis on PG

| | Plant | 16:0 | 16:1t | 16:1c | 18:0 | 18:1 | 18:2 | 18:3 | Σ 16:0 + 18:0 + 16:1t |
|---|---|---|---|---|---|---|---|---|---|
| PG | Control plant | 32 | 37 | 0 | 1 | 5 | 10 | 14 | 70 |
| | Transformed plant | 18 | 37 | 8 | 0 | 10 | 12 | 15 | 55 |

TABLE 4

Results of fatty acid analysis on other lipids

| | Plant | 16:0 | 16:1 | 16:2 | 16:3 | 18:0 | 18:1 | 18:2 | 18:3 | Σ 16:0 + 18:0 |
|---|---|---|---|---|---|---|---|---|---|---|
| SQDG | Control plant | 51 | 1 | 0 | 0 | 3 | 2 | 7 | 36 | 54 |
| | Transformed plant | 36 | 22 | 0 | 0 | 0 | 4 | 9 | 28 | 36 |
| MGDG | Control plant | 7 | 0 | 1 | 9 | 1 | 2 | 4 | 76 | 8 |
| | Transformed plant | 3 | 9 | 1 | 10 | 0 | 1 | 5 | 69 | 3 |
| DGDG | Control plant | 19 | 0 | 0 | 0 | 3 | 1 | 4 | 73 | 22 |
| | Transformed plant | 9 | 13 | 0 | 1 | 0 | 1 | 5 | 70 | 9 |
| PC | Control plant | 28 | 0 | 0 | 0 | 5 | 1 | 21 | 44 | 33 |
| | Transformed plant | 19 | 12 | 0 | 0 | 3 | 4 | 40 | 23 | 22 |
| PE | Control plant | 20 | 0 | 0 | 0 | 3 | 1 | 6 | 70 | 23 |
| | Transformed plant | 18 | 10 | 0 | 0 | 2 | 2 | 31 | 38 | 20 |
| PI | Control plant | 48 | 1 | 0 | 0 | 2 | 1 | 11 | 37 | 50 |
| | Transformed plant | 44 | 7 | 0 | 0 | 1 | 2 | 18 | 28 | 45 |

The results of the analysis of PG-bound fatty acids revealed that in the transformed tobacco plants expressing *Anacystis nidulans*-derived fatty acid desaturase, 16:0 (palmitic acid) decreased greatly whereas 16:1 cis increased and 18:0 became almost zero (a small amount of 18:0 was present in the control) whereas 18:1 increased. Hence, the content of saturated fatty acids (16:0+16:1trans+18:0(stearic acid)) was 70% in the control tobacco plants whereas it was significantly reduced to 55% in the tobacco plants transformed with the desturase gene. The results of the respective analyses on PG at the sn-1 and sn-2 positions revealed that more than 98% of the sn-2 position was occupied with saturated fatty acids (16:0 or 16:1trans) and that all of the 16:1 newly produced by gene introduction was present at the sn-1 position. Hence, it is clear that the amount of saturated fatty acids at the sn-1 position of PG became extremely small in the tobacco transformed with the desaturase gene. In conclusion, it was found that the amount of saturated molecular species consisting of saturated fatty acids at both sn-1 and 2 positions decreased greatly and that, therefore, the tobacco plants changed into a significantly chilling-resistant type as estimated from the composition of molecular species of the lipids.

In this example, the results of lipid analysis of the transformed tobacco plants demonstrated that the *Anacystis nidulans*-derived fatty acid desaturase could desaturate 16:0 and 18:0 in almost all lipids with an extremely high efficiency in the transformed tobacco which is a higher plant.

The results of fatty acid analysis on total root lipids are shown in Table 5.

TABLE 5

| Plant | Results of fatty acid analysis on total root lipids | | | | | | | | |
|---|---|---|---|---|---|---|---|---|---|
| | 16:0 | 16:1 | 16:2 | 16:3 | 18:0 | 18:1 | 18:2 | 18:3 | Σ 16:0 + 18:0 |
| Non-transformed plant | 26 | 0 | 0 | 0 | 5 | 2 | 47 | 21 | 31 |
| Transformed plant | 17 | 13 | 0 | 0 | 2 | 4 | 58 | 6 | 19 |

The results revealed that surprisingly enough, the *Anacystis nidulans*-derived fatty acid desaturase catalyzed the desaturation of 16:0 and 18:0 in not only leaves but also roots, suggesting that the fatty acid desaturase gene of the present invention should have not only the possibility of improving the chilling resistance of plants but also the possibility of increasing the content of unsaturated fatty acids and that it is useful in industries where plants are used as raw materials for oil production.

EXAMPLE 7

Testing the Transformed Tobacco Plants for Chilling Resistance

The transformants estimated to be promising in the RNA expression assay and the lipid analyses were self-pollinated and the seeds of next generation were collected. Part of the seeds were planted in an MS-HF medium supplemented with 800 ppm kanamycin and cultured at 25° C. for 2 weeks under the conditions of 16 hours under light and 8 hours in the dark. Kanamycin-tolerant seedlings were selected. The seedlings were transplanted in plant boxes and cultured for an additional 4 weeks. In regard to the plant transformed with pBI121, the above procedure was repeated (control).

The plants were subjected to a low temperature treatment at 4° C. under continuous light for 11 days and then cultured at 25° C. for 2 days. As a result, marked leaf waving and chlorosis were observed in the control plants (the plant transformed with pBI121) but no injury was observed in the transformed plants. Hence, it was assumed that the chilling resistance was improved by introduction of the desaturase gene.

INDUSTRIAL APPLICABILITY

Chilling resistance can be imparted to plants and their content of unsaturated fatty acids can be increased by introducing the gene of the present invention which encodes the Δ9 desaturase.

We claim:

1. An isolated polynucleotide molecule encoding a protein having an activity of desaturating lipid-bound fatty acids at the Δ9 position, wherein said polynucleotide molecule comprises a nucleotide sequence that is present in the genus Anacystis and that hybridizes to a probe having a nucleotide the sequence of SEQ ID NO:1 or SEQ ID NO:3 under (A) an incubation condition of 55° C. for 16 hours in a solution consisting of 6×SSPE, 02% SDS and 100 g/ml herring sperm DNA, and (B) washing condition of twice for 15 minutes each in 2×SSC at room temperature.

2. A polynucleotide molecule encoding a protein having an activity of desaturating lipid-bound fatty acids at the Δ9 position, wherein said protein comprises the amino acid sequence shown in SEQ ID NO:4.

3. A polynucleotide molecule encoding a protein having an activity of desaturating lipid-bound fatty acids at the Δ9 position, wherein the polynucleotide molecule comprises the nucleotide sequence of SEQ ID NO: 3.

4. A vector which contains the polynucleotide molecule that encodes a protein having an activity of desaturating lipid-bound fatty acids at the Δ9 position according to any one of claims 1–3.

5. A plant cell transformed with the polynucleotide molecule that encodes a protein having an activity of desaturating lipid-bound fatty acids at the Δ9 position according to any one of claims 1–3.

6. A method for creating a plant by regenerating the plant cell of claim 5 to produce a mature plant.

7. A plant transformed with the polynucleotide molecule that encodes a protein having an activity of desaturating lipid-bound fatty acids at the Δ9 position according to any one of claims 1–3.

8. A method for creating a plant cell having an improved chilling-resistance, which comprises introducing a polynucleotide molecule that is present in the genus Anacystis and that encodes a Δ9 desaturase having an activity of desaturating lipid-bound fatty acids at the Δ9 position.

9. A method for creating a plant having an improved chilling-resistance, which comprises introducing a polynucleotide molecule that is present in the genus Anacystis and that encodes a Δ9 desaturase having an activity of desaturating lipid-bound fatty acids at the Δ9 position.

* * * * *

UNITED STATES PATENT AND TRADEMARK OFFICE

CERTIFICATE OF CORRECTION

PATENT NO. : 6,043,411
DATED : March 28, 2000
INVENTOR(S) : Nishizawa, et al.

It is certified that error appears in the above-identified patent and that said Letters Patent is hereby corrected as shown below:

Please note on the title page of the patent:

Claim 1,
Line 2, contains a typographical error wherein "02% SDS and 100 g/ml" should read "-- 0.2% SDS and 100 u g/ml--.

Signed and Sealed this

Twenty-first Day of August, 2001

*Attest:*

Nicholas P. Godici

NICHOLAS P. GODICI

*Attesting Officer* *Acting Director of the United States Patent and Trademark Office*

```
                         SEQUENCE LISTING


(1) GENERAL INFORMATION:

   (iii) NUMBER OF SEQUENCES: 12


(2) INFORMATION FOR SEQ ID NO:1:

     (i) SEQUENCE CHARACTERISTICS:
          (A) LENGTH: 196 base pairs
          (B) TYPE: nucleic acid
          (C) STRANDEDNESS: double
          (D) TOPOLOGY: linear

    (vi) ORIGINAL SOURCE:
          (A) ORGANISM: Anabaena variabilis
          (B) STRAIN: IAM M-3

    (xi) SEQUENCE DESCRIPTION: SEQ ID NO:1:

GCTCTGGGGT TGTTGCTGTT ATATCTAGGC GGGTGGTCTT TTGTGGTCTG GGGAGTTTTC     60

TTTCGCATCG TTTGGGTTTA CCACTGTACT TGGTTGGTAA ACAGCGCTAC CCATAAGTTT    120

GGCTACCGCA CCTATGATGC TGGTGACAGA TCCACTAACT GTTGGTGGGT AGCTGTCCTA    180

GTGTTTGGTG AAGGTT                                                    196


(2) INFORMATION FOR SEQ ID NO:2:

     (i) SEQUENCE CHARACTERISTICS:
          (A) LENGTH: 65 amino acids
          (B) TYPE: amino acid
          (C) STRANDEDNESS:
          (D) TOPOLOGY: linear

    (vi) ORIGINAL SOURCE:
          (A) ORGANISM: Anabaena variabilis
          (B) STRAIN: IAM M-3
```

-continued (xi) SEQUENCE DESCRIPTION: SEQ ID NO:2:

```
Ala Leu Gly Leu Leu Leu Leu Tyr Leu Gly Gly Trp Ser Phe Val Val
1               5                   10                  15

Trp Gly Val Phe Phe Arg Ile Val Trp Val Tyr His Cys Thr Trp Leu
            20                  25                  30

Val Asn Ser Ala Thr His Lys Phe Gly Tyr Arg Thr Tyr Asp Ala Gly
        35                  40                  45

Asp Arg Ser Thr Asn Cys Trp Trp Val Ala Val Leu Val Phe Gly Glu
    50                  55                  60

Gly
 65
```

(2) INFORMATION FOR SEQ ID NO:3:

(i) SEQUENCE CHARACTERISTICS:
(A) LENGTH: 837 base pairs
(B) TYPE: nucleic acid
(C) STRANDEDNESS: double
(D) TOPOLOGY: linear (vi) ORIGINAL SOURCE:
(A) ORGANISM: Anacystis nidulans
(B) STRAIN: R2-SPc (xi) SEQUENCE DESCRIPTION: SEQ ID NO:3:

```
ATGACCCTTG CTATCCGACC CAAGCTTGCC TTCAACTGGC CGACCGCCCT GTTCATGGTC     60

GCCATTCACA TTGGAGCACT GTTAGCGTTC CTGCCGGCCA ACTTTAACTG GCCCGCTGTG    120

GGCGTGATGG TTGCGCTGTA TTACATTACC GGTTGTTTTG GCATCACCCT AGGCTGGCAC    180

CGGCTAATTT CGCACCGTAG CTTTGAAGTT CCCAAATGGC TGGAATACGT GCTGGTGTTC    240

TGTGGCACCT TGGCCATGCA GCACGGCCCG ATCGAATGGA TCGGTCTGCA CCGCCACCAT    300

CACCTCCACT CTGACCAAGA TGTCGATCAC CACGACTCCA ACAAGGGTTT CCTCTGGAGT    360

CACTTCCTGT GGATGATCTA CGAAATTCCG GCCCGTACGG AAGTAGACAA GTTCACGCGC    420

GATATCGCTG GCGACCCTGT CTATCGCTTC TTTAACAAAT ATTTCTTCGG TGTCCAAGTC    480

CTACTGGGGG TACTTTTGTA CGCCTGGGGC GAGGCTTGGG TTGGCAATGG CTGGTCTTTC    540

GTCGTTTGGG GGATCTTCGC CCGCTTGGTG GTGGTCTACC ACGTCACTTG GCTGGTGAAC    600

AGTGCTACCC ACAAGTTTGG CTACCGCTCC CATGAGTCTG GCGACCAGTC CACCAACTGC    660

TGGTGGGTTG CCCTTCTGGC CTTTGGTGAA GGCTGGCACA ACAACCACCA CGCCTACCAG    720

TACTCGGCAC GTCATGGCCT GCAGTGGTGG GAATTTGACT TGACTTGGTT GATCATCTGC    780

GGCCTGAAGA AGGTGGGTCT GGCTCGCAAG ATCAAAGTGG CGTCTCCAAA CAACTAA       837
```

(2) INFORMATION FOR SEQ ID NO:4:

(i) SEQUENCE CHARACTERISTICS:
(A) LENGTH: 278 amino acids
(B) TYPE: amino acid
(C) STRANDEDNESS:
(D) TOPOLOGY: linear (vi) ORIGINAL SOURCE:
(A) ORGANISM: Anacystis nidulans
(B) STRAIN: R2-SPc (xi) SEQUENCE DESCRIPTION: SEQ ID NO:4:

```
Met Thr Leu Ala Ile Arg Pro Lys Leu Ala Phe Asn Trp Pro Thr Ala
1               5                   10                  15
```

-continued

```
Leu Phe Met Val Ala Ile His Ile Gly Ala Leu Leu Ala Phe Leu Pro
            20                  25                  30

Ala Asn Phe Asn Trp Pro Ala Val Gly Val Met Val Ala Leu Tyr Tyr
        35                  40                  45

Ile Thr Gly Cys Phe Gly Ile Thr Leu Gly Trp His Arg Leu Ile Ser
    50                  55                  60

His Arg Ser Phe Glu Val Pro Lys Trp Leu Glu Tyr Val Leu Val Phe
65                  70                  75                  80

Cys Gly Thr Leu Ala Met Gln His Gly Pro Ile Glu Trp Ile Gly Leu
                85                  90                  95

His Arg His His His Leu His Ser Asp Gln Asp Val Asp His His Asp
            100                 105                 110

Ser Asn Lys Gly Phe Leu Trp Ser His Phe Leu Trp Met Ile Tyr Glu
        115                 120                 125

Ile Pro Ala Arg Thr Glu Val Asp Lys Phe Thr Arg Asp Ile Ala Gly
    130                 135                 140

Asp Pro Val Tyr Arg Phe Phe Asn Lys Tyr Phe Phe Gly Val Gln Val
145                 150                 155                 160

Leu Leu Gly Val Leu Leu Tyr Ala Trp Gly Glu Ala Trp Val Gly Asn
                165                 170                 175

Gly Trp Ser Phe Val Val Trp Gly Ile Phe Ala Arg Leu Val Val Val
            180                 185                 190

Tyr His Val Thr Trp Leu Val Asn Ser Ala Thr His Lys Phe Gly Tyr
        195                 200                 205

Arg Ser His Glu Ser Gly Asp Gln Ser Thr Asn Cys Trp Trp Val Ala
    210                 215                 220

Leu Leu Ala Phe Gly Glu Gly Trp His Asn Asn His His Ala Tyr Gln
225                 230                 235                 240

Tyr Ser Ala Arg His Gly Leu Gln Trp Trp Glu Phe Asp Leu Thr Trp
                245                 250                 255

Leu Ile Ile Cys Gly Leu Lys Lys Val Gly Leu Ala Arg Lys Ile Lys
            260                 265                 270

Val Ala Ser Pro Asn Asn
        275
```

(2) INFORMATION FOR SEQ ID NO:5:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:5:

ATGACAATTG CTACTTCA 18

(2) INFORMATION FOR SEQ ID NO:6:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

-continued (xi) SEQUENCE DESCRIPTION: SEQ ID NO:6:

GCTCTGGGGT TGTTG 15

(2) INFORMATION FOR SEQ ID NO:7:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:7:

CAACAACCCC AGAGC 15

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:8:

RTGRTGRTTR TTRTGCCA 18

(2) INFORMATION FOR SEQ ID NO:9:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:9:

ACGTCATGGC CTGCAGT 17

(2) INFORMATION FOR SEQ ID NO:10:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:10:

CGCGGATCCT TAGTTGTTTG GAGACG 26

(2) INFORMATION FOR SEQ ID NO:11:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

-continued

```
    (xi) SEQUENCE DESCRIPTION: SEQ ID NO:11:

CATATGACCC TTGCTATCCG ACCCA                                        25


(2) INFORMATION FOR SEQ ID NO:12:

     (i) SEQUENCE CHARACTERISTICS:
          (A) LENGTH: 29 base pairs
          (B) TYPE: nucleic acid
          (C) STRANDEDNESS: single
          (D) TOPOLOGY: linear

    (ii) MOLECULE TYPE: other nucleic acid
          (A) DESCRIPTION: /desc = "synthetic DNA"

    (xi) SEQUENCE DESCRIPTION: SEQ ID NO:12:

AGCTTGGGTC GGATAGCAAG GGTCATATG                                    29
```